United States Patent [19]

Ford et al.

[11] 4,316,841

[45] Feb. 23, 1982

[54] REFORMING LINEAR POLYAMINES

[75] Inventors: Michael E. Ford, Trexlertown; Thomas A. Johnson, Orefield, both of Pa.

[73] Assignee: Air Products and Chemicals, Inc., Allentown, Pa.

[21] Appl. No.: 214,396

[22] Filed: Dec. 8, 1980

[51] Int. Cl.³ .................... C07C 85/00; C07C 85/20; C07D 241/04; C07D 295/12
[52] U.S. Cl. .................... 260/239 BC; 544/358; 544/402; 564/511; 564/512
[58] Field of Search ............... 564/511, 512; 544/358, 544/402; 260/239 BC

[56] References Cited

U.S. PATENT DOCUMENTS

| | | | |
|---|---|---|---|
| T945,004 | 4/1976 | Valaitis et al. | 564/511 |
| 3,217,028 | 11/1965 | Vertnik | 564/511 |

FOREIGN PATENT DOCUMENTS 1500220  2/1978  United Kingdom ................ 564/511

OTHER PUBLICATIONS

Genty, "Chemical Abstracts", vol. 72, Ab. No. 113505y, (1970).

*Primary Examiner*—John Doll
*Attorney, Agent, or Firm*—Russell L. Brewer; E. Eugene Innis; James C. Simmons

[57] ABSTRACT

Process for production of polyalkylene polyamines, preferably non-cyclic polyalkylene polyamines, by reforming of other polyalkylene polyamines. The reforming process is effected by reacting the polyalkylene polyamine starting material in the presence of a phosphate, preferably a boron phosphate, catalyst at elevated temperature and pressure and in the presence of sufficient water and sufficient catalyst, for a reaction period and under reaction conditions otherwise adapted to bring about the desired reforming reaction.

9 Claims, No Drawings

REFORMING LINEAR POLYAMINES

TECHNICAL FIELD

This invention pertains to the catalyzed reforming of alkylene polyamines to other, preferably higher and preferably non-cyclic, polyalkylene polyamines.

BACKGROUND OF PRIOR ART

Various processes and catalysts have been disclosed for producing polyalkylene polyamines, including those disclosed in the patents listed below. These listed U.S. patents have been considered with reference to patentability of the invention disclosed and claimed herein. However, they are not considered sufficiently relevant for separate comment.

U.S. Pat. No. 4,103,087, Brennan
U.S. Pat. No. 4,123,462, Best
U.S. Pat. No. 4,061,633, Blyakhman et al
U.S. Pat. No. 3,270,059, Winderl et al
U.S. Pat. No. 3,037,023, Moss et al
U.S. Pat. No. 3,565,957, Mirviss et al
U.S. Pat. No. 3,281,470, Vertnik
U.S. Pat. No. 2,519,803, Weber et al
U.S. Pat. No. 3,255,248, Suesengoth et al
U.S. Pat. No. 3,427,356, Baer et al With regard to the preparation of higher polyalkylene polyamines by reaction of ethylene diamine or lower polyalkylene polyamines, British Pat. No. 1,500,220 of the Texaco Development Corporation is of specific interest. According to that patent, predominantly non-cyclic polyamines are formed by reaction of lower polyalkylene polyamines with alkanol amines under elevated temperature and pressure conditions, with a phosphorus-containing catalyst. Among the suitable catalysts are "acidic metal phosphates [including] boron phosphate, ferric phosphate, and aluminum phosphate", (Col. 3, lines 27-29). That patent further teaches, and Examples II and III thereof demonstrate, that the process there taught requires "an alkylating material such as an ethanolamine compound in the process of the invention", (Col. 5, lines 55-59).

With this background in mind, it is the general object of the present invention to provide a practical and economical process for producing various polyalkylene polyamines.

BRIEF SUMMARY OF INVENTION

In accordance with the process of the present invention, various polyalkylene polyamines may be produced by a reforming reaction, by contacting another polyalkylene polyamine or ethylene diamine starting material with water, in the presence of a phosphate catalyst, at elevated temperature and pressure, the temperature, pressure, catalyst, catalyst and water amounts, and time of reaction being adapted to permit the starting material to be reformed into some other, preferably a non-cyclic and higher molecular weight, polyalkylene polyamine.

The preferred starting materials, for producing higher non-cyclic polyalkylene polyamines, are ethylenediamine and homologues thereof, particularly including diethylenetriamine and triethylenetetramine.

While boron phosphate is the preferred catalyst, various metal phosphates are also effective. Iron, zinc, and aluminum phosphate catalysts, in particular, are known to be effective. Other metal phosphates which may be used are the phosphates of lithium, sodium, potassium, and other metals of group IA of the periodic table; beryllium, magnesium, calcium, and other metals of group IIA of the periodic table; zirconium, antimony, tin (valence states II and IV) and iron in both the ferrous and ferric states.

In general, the reaction time is on the order of 0.5 to 5 hours (preferably 1-4 hours), the reaction temperature range is 200°-400° C. (preferably 225°-350° C.), the proportion of water present, in weight percent based on the amount of starting material, is 3-20%, and the amount of catalyst present, in mol percent based on amount of starting material present, is 2-20%, preferably 3-10% (the catalyst amount being recited for a batch process; in a continuous process, contact time may be selected to produce effectively the same degree of catalyzation, a factor which would have to be determined experimentally for the particular process involved).

BRIEF DESCRIPTION OF THE INVENTION

In contrast to the prior art which suggests that boron phosphate-catalyzed ethylenediamine would be non-reactive at elevated temperature and pressure, in the absence of an alkanol amine, the present invention comprises a process wherein reformation of ethylene diamine or polyalkylene polyamines is effected by contact thereof with a phosphate catalyst preferably boron phosphate, in the presence of water and at elevated temperature and pressure. By way of detailed description of this invention, reference is made to the examples which follow, and the related tables in which are listed polyalkylene polyamine compounds, in which listing the starting material in each example is noted, along with the weight percent of other polyalkylene polyamines produced, based on the weight of starting material.

Following is a description of four experiments, the first three of which confirm, consistent with British Pat. No. 1,500,220 teaching, that ethylenediamine will not reform into other polyalkylene polyamines at 275° C., even in the presence of boron phosphate catalyst, unless sufficient catalyst and water are present. The fourth of these experiments demonstrates, by comparison to Experiment 3, that by the inclusion of substantially more catalyst than was present in Experiment 3, conversion of ethylenediamine to piperazine and to aminoethyl piperazine was effected.

Experiment 1

Ethylenediamine (390 mg; $6.5 \times 10^{-3}$ mol) was placed in a two milliliter reactor and heated at 275° C. for 2.0 hours with agitation. During this period, internal pressure of 200-300 psi developed. Cooling to room temperature and gas liquid chromatography (glc) analysis of the reaction mixture indicated that no reaction had occurred (see Table I).

Experiment 2

A mixture of ethylenediamine (390 mg; $6.5 \times 10^{-3}$ mol) and dry boron phosphate (20 mg; $1.95 \times 10^{-4}$ mol) was placed in a two milliliter reactor and heated at 275° C. for two hours. During this period, internal pressure of 200-300 psi developed. Cooling to room temperature and glc analysis of the reaction mixture indicated that no reaction had occurred (see Table I).

Experiment 3

The procedure of Example II of British Pat. No. 1,500,220 was repeated. Specifically, 400 gm of an aqueous solution of ethylenediamine (91 wt % diamine, 9 wt % water, 6.1 mol ethylenediamine) and 20 gm (0.18 mol, 3 mol %) boron phosphate were charged to a dry nitrogen purged 1 liter stainless steel autoclave equipped with stirring means and pre-pressured with nitrogen, the reactant mixture then being heated at a temperature of 275° C.–280° C. under a pressure of 525–560 psig for 2.0 hours. The reactant mixture was than analyzed by gas liquid chromatography after cooling to room temperature and no reaction of ethylenediamine to form higher polyamines was observed (see Table I).

Experiment 4

The procedure of Experiment 3 was repeated with inclusion of five times the original amount of boron phosphate. Conversion of ethylenediamine to piperazine and N-(2-aminoethyl)piperazine was observed (see Table I).

TABLE I[(a)]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 1 | 0 | 0 | * | 0.00 | 0.00 | 0.00 | 0.00 | 0.00 | 0.00 | 0.00 | — |
| 2 | 3 | 0 | * | 0.00 | 0.00 | 0.00 | 0.00 | 0.00 | 0.00 | 0.00 | — |
| 3 | 3 | 9 | * | 0.00 | 0.00 | 0.00 | 0.00 | 0.00 | 0.00 | 0.00 | — |
| 4 | 15 | 9 | * | 5.41 | 2.78 | 0.00 | 0.00 | 0.00 | 0.00 | 0.00 | — |

[a]Weight percent of components in product on feedstock-free basis. Catalyst and water incorporations are based on polyamine feedstock.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*Starting material The foregoing experiments were all conducted at 275° C. By comparison, the following experiments were conducted at higher temperatures and with varying amounts of water and reaction time to illustrate the effect on the reaction product of these variables.

Experiment 5

Ethylenediamine (390 mg; $6.5 \times 10^{-3}$ mol) was placed in a two milliliter reactor and heated at 300° C. for 2 hours with agitation. During this period, internal pressure of 200–300 psi developed. Cooling to room temperature and gas liquid chromatography (glc) analysis of the reaction mixture indicated that no reaction had occurred (see Table II).

Experiment 6

The procedure of Experiment 5 was repeated, with the process being carried out for 3 hours. Glc analysis of the cooled reaction mixture indicated that no reaction had occurred (see Table II).

Experiment 7

A mixture of ethylenediamine (390 mg; $6.5 \times 10^{-3}$ mol) and dry boron phosphate (45 mg; $4.29 \times 10^{-4}$ mol, 6.6 mol %, based on ethylenediamine) was heated at 300° C. for 3 hours with agitation. During this period, internal pressure of 200–300 psi developed. Cooling to room temperature and glc analysis of the reaction mixture indicated that essentially no reaction had occurred (see Table II).

Experiment 8

A mixture of ethylenediamine (90.0 gm, 1.47 mol) and freshly prepared boron phosphate (8.3 gm, 5.3 mol %, based on ethylenediamine) was stirred in a closed autoclave. The boron phosphate also contained water (4.21 gm; $2.34 \times 10^{-1}$ mol, 4.7 weight %, based on ethylenediamine feed). The mixture was heated to 300° C. with stirring for 1 hour. Cooling to room temperature and glc analysis of the reaction mixture indicated substantial conversion of ethylenediamine to a mixture of higher polyamines (see Table II).

Experiment 9

The procedure of Experiment 8 was repeated with heating of the reaction for 3 hours. Cooling to room temperature and glc anaylsis of the reaction mixture indicated substantial conversion of ethylenediamine to a mixture of higher polyamines (see Table II).

Experiment 10

The procedure of Experiment 8 was repeated with heating of the reaction for 5 hours. Glc analysis of the cooled reaction mixture indicated substantial conversion of ethylenediamine to a mixture of higher polyamines (see Table II).

Experiment 11

A mixture of ethylenediamine (390 mg; $6.5 \times 10^{-3}$), dry boron phosphate (34 mg; $3.25 \times 10^{-4}$ mol, 5 mol % based on ethylenediamine) and water (35 mg; $1.94 \times 10^{-3}$ mol, 9 weight % based on ethylenediamine) was placed in a two milliliter reactor and heated at 300° C. for 3 hours with agitation. Cooling to room temperature and glc analysis of the reaction mixture indicated that N-(2-aminoethyl)piperazine and diethylenetriamine had been formed (see Table II).

Experiment 12

A mixture of ethylenediamine (72.5 gm, 1.19 mol), freshly prepared boron phosphate (8.3 gm; 6.6 mol %, based on ethylenediamine), containing 4.3 gm water and additional water (17.5 gm, 0.97 mol), was stirred in a closed autoclave. The total amount of water, with the boron phosphate catalyst (4.24 gm) and the feedstock (17.5 gm) was 21.74 gm (1.20 mol; 30 weight %, based on ethylenediamine). The mixture was heated at 300° C. with stirring for 3 hours. Cooling to room temperature and glc analysis of the reaction mixture indicated substantial conversion of ethylenediamine to a mixture of higher polyamines (see Table II).

This group of experiments demonstrates three facets of polyamine reforming:

(1) The necessity for inclusion of water in the reaction mixture in order to obtain polyamine reforming (cf Experiments 5 and 6 with Experiments 7–12);
(2) The ease with which polyamine reforming can occur at 300° C. vs. 275° C. (cf Experiments 8–10 with Experiments 3 and 4); and
(3) The decrease in selectivity to non-cyclic products of polyamine reforming with increasing reaction time (Experiments 8–10). This is significant since conversion to non-cyclic products is of particular interest because of the greater commercial value of such products, as compared to cyclic polyalkylene polyamines generally.

mol %, based on ethylenediamine) and water (35 mg; $1.94 \times 10^{-3}$ mol, 9 weight %, based on ethylenediamine) was placed in a two milliliter reactor and heated at 325° C. with agitation for 2 hours. Cooling to room temperature and glc analysis of the reaction mixture indicated that a mixture of higher polyamines had been formed (see Table III).

Experiment 15

A mixture of ethylenediamine (90.0 gm; 1.47 mol) and freshly prepared boron phosphate (8.3 gm; 5.3 mol %, based on ethylenediamine) was stirred in a closed autoclave. The boron phosphate also contained water (4.21 gm; $2.34 \times 10^{-1}$ mol, 4.7 weight % based on ethylenediamine). The mixture was heated to 350° C. with stirring for 2 hours. Cooling to room temperature and glc analysis indicated substantial conversion of ethylenediamine to a mixture of higher polyamines (see Table III).

TABLE II[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 5 | 0 | 0 | * | 0.00 | 0.00 | 0.00 | 0.00 | 0.00 | 0.00 | 0.00 | — |
| 6 | 3 | 0 | * | 0.00 | 0.00 | 0.00 | 0.00 | 0.00 | 0.00 | 0.00 | — |
| 7 | 6.6 | 0 | * | 0.00 | 0.13 | 0.00 | 0.00 | 0.00 | 0.00 | 0.00 | — |
| 8 | 5.3 | 4.7 | * | 0.47 | 0.34 | 15.28 | 0.58 | 2.63 | 0.00 | 0.00 | 82 |
| 9 | 5.3 | 4.7 | * | 2.40 | 1.40 | 9.90 | 4.50 | 1.60 | 0.00 | 0.00 | 73 |
| 10 | 5.3 | 4.7 | * | 5.70 | 2.90 | 11.80 | 7.50 | 3.70 | 4.60 | 3.80 | 60 |
| 11 | 5.0 | 9.0 | * | 0.00 | 0.39 | 0.07 | 0.00 | 0.00 | 0.00 | 0.00 | 15 |
| 12 | 6.6 | 19.4 | * | 0.91 | 0.34 | 3.62 | 0.21 | 0.00 | 0.00 | 0.00 | 75 |

[a]Weight percent of components in product on feedstock-free basis. Catalyst and water incorporations are based on polyamine feedstock.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*Starting material TABLE III[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 13 | 0 | 0 | * | 0.00 | 0.00 | 0.00 | 0.00 | 0.00 | 0.00 | 0.00 | 0 |
| 14 | 5 | 9 | * | 0.80 | 0.84 | 0.74 | 1.44 | 1.18 | 0.00 | 0.36 | 41 |
| 15 | 5.3 | 4.7 | * | 10.66 | 1.30 | 2.34 | 1.33 | 7.12 | 0.00 | 0.00 | 16 |

[a]Weight percent of components in product on feedstock-free basis. Catalyst and water incorporations are based on polyamine feedstock.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*Starting material The following three experiments illustrate the reforming of EDA, in accordance with the present invention, at temperatures over 300° C.

Experiment 13

Ethylenediamine (390 mg; $6.5 \times 10^{-3}$ mol) was placed in a two milliliter reactor and heated at 325° C. for two hours with agitation. Cooling to room temperature and glc analysis of the reaction mixture showed that no reaction had occurred (see Table III).

Experiment 14

A mixture of ethylenediamine (390 mg; $6.5 \times 10^{-3}$ mol), dry boron phosphate (34 mg; $3.25 \times 10^{-4}$ mol, 5

From the foregoing, it appears that a moderate elevation in temperature induces the desired reforming reaction, and the tendency toward the preferred non-cyclic products, even in the range of catalyst level and water content comparable to that reported upon in Experiments 1–4 above.

That diethylenetriamine may also be reformed in accordance with the present invention, is shown in Experiments 16–18.

Experiment 16

Diethylenetriamine (670 mg; $6.5 \times 10^{-3}$ mol) was placed in a two milliliter reactor and heated at 275° C.

with agitation for 3 hours. Cooling to room temperature and glc analysis indicated that essentially no reaction had occurred (see Table IV).

Experiment 17

A mixture of diethylenetriamine (670 mg; $6.5 \times 10^{-3}$ mol) and freshly prepared boron phosphate (8.9 mg; $8.25 \times 10^{-5}$ mol, 1.25 mol % based on diethylenetriamine) was placed in a two milliliter reactor. The boron phosphate also contained water (0.4 mg; $2.44 \times 10^{-4}$ mol, 0.65 weight %, based on diethylenetriamine). The mixture was heated at 275° C. with agitation for 3 hours. Cooling to room temperature and glc analysis indicated that substantial conversion of diethylenetriamine to a mixture of polyamines had occurred (see Table IV).

Experiment 18

A mixture of diethylenetriamine (101 gm; 1.0 mol) and freshly prepared boron phosphate (8.3 gm; $7.8 \times 10^{-2}$ mol, 7.8 mol %, based on diethylenetriamine) was stirred in a closed autoclave. The boron phosphate also contained water (4.2 gm; $2.34 \times 10^{-1}$ mol, 4.2 weight %, on diethylenetriamine). The mixture was heated at 275° C. for 3 hours. Cooling to room temperature and glc analysis indicated that substantial conversion of diethylenetriamine to mixture of polyamines had occurred (see Table IV).

Experiment 20

A mixture of ethylenediamine (390 mg; $6.5 \times 10^{-3}$ mol) and zinc phosphate (125 mg; $2.7 \times 10^{-4}$ mol, 4.5 mol %, based on ethylenediamine) was placed in a two milliliter reactor. The zinc phosphate contained water (14.5 mg; $8.09 \times 10^{-4}$ mol, 3.7 weight %, based on ethylenediamine) as water of hydration. The mixture was heated at 300° C. with agitation for two hours. Cooling to room temperature and glc analysis of the reaction mixture indicated that a mixture of piperazine and N-(2-aminoethyl)piperazine had been formed (see Table V).

Experiment 21

A mixture of diethylenetriamine (670 mg; $6.5 \times 10^{-3}$ mol) and iron phosphate (100 mg; $5.4 \times 10^{-4}$ mol, 8.3 mol %, based on diethylenetriamine) was placed in a two milliliter reactor. The iron phosphate contained water (29 mg; $1.62 \times 10^{-3}$ mol, 4.3 weight percent based on diethylenetriamine). The mixture was heated at 275° C. with agitation for 3 hours. Cooling to room temperature and glc analysis indicated that substantial conversion of diethylenetriamine to a mixture of polyamines had occurred (see Table V).

TABLE IV[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 16 | 0 | 0 | 0.13 | 0.00 | 0.54 | * | 0.00 | 0.00 | 0.00 | 0.00 | — |
| 17 | 1.25 | 0.65 | 0.79 | 0.24 | 0.90 | * | 1.15 | 0.21 | 0.00 | 0.00 | 59 |
| 18 | 7.8 | 4.2 | 5.20 | 1.70 | 1.50 | * | 3.90 | 1.20 | 7.90 | 1.50 | 76 |

[a]Weight percent of components in product on feedstock-free basis. Catalyst and water incorporations are based on polyamine feedstock.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*Starting material Phosphates other than boron phosphates are also effective catalysts in the process of the present invention, as illustrated by Experiments 19–22, below.

Experiment 19

A mixture of ethylenediamine (390 mg; $6.5 \times 10^{-3}$ mol) and iron phosphate (100 mg; $5.4 \times 10^{-3}$ mol, 8.3 mol %, based on ethylenediamine) was placed in a two milliliter reactor. The iron phosphate contained water (29 mg; $1.62 \times 10^{-3}$ mol, 7.4 weight %, based on ethylenediamine) as water of hydration. The mixture was heatedl at 300° C. with agitation for 2 hours. Cooling to

Experiment 22

A mixture of diethylenetriamine (670 mg; $6.5 \times 10^{-3}$ mol), aluminum phosphate (65 mg; $5.4 \times 10^{-4}$ mol, 8.3 mol %, based on diethylenetriamine) and water (40 mg; $2.24 \times 10^{-3}$ mol, 6 weight %, based on diethylenetriamine) was placed in a two milliliter reactor and heated at 275° C. with agitation for 3 hours. Cooling to room temperature and glc analysis indicated that substantial conversion of diethylenetriamine to a mixture of polyamines had occurred (see Table V).

TABLE V[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 19 | 8.3 | 4.98 | * | 1.54 | 0.82 | 0.00 | 0.00 | 0.72 | 0.00 | 0.00 | 0 |
| 20 | 4.15 | 3.72 | * | 3.81 | 2.03 | 0.00 | 0.00 | 0.00 | 0.00 | 0.00 | 0 |
| 21 | 8.3 | 4.3 | 20.61 | 0.89 | 14.88 | * | 0.00 | 0.00 | 0.00 | 0.00 | 57 |

TABLE V(a)-continued

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 22 | 8.3 | 6.0 | 1.26 | 0.00 | 6.30 | * | 0.00 | 2.52 | 0.00 | 0.00 | 12 |

[a]Weight percent of components in product on feedstock-free basis. Catalyst and water incorporations are based on polyamine feedstock.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*Starting material By way of generalization, the foregoing exemplification of other metal phosphates which may be used as catalysts in the present invention, namely iron, zinc and aluminum, are considered representative of a much larger group of metals that may be used, including lithium, sodium, potassium, and other metals of group IA of the periodic table; beryllium, magnesium, calcium, and other metals of group IIA of the periodic table; zirconium, antimony, tin (valence states II and IV) and iron in both the ferrous and ferric states.

More generally, while this invention has been described with respect to specific embodiments thereof, it is not limited thereto and the appended claims are intended to be construed to include not only the specific embodiments described or referred to, but to such other embodiments of the invention as may be devised by those skilled in the art.

INDUSTRIAL APPLICATION OF THE INVENTION

This invention may be used to produce polyalkylene polyamine reactants having a variety of industrial applications, and particularly to produce from other lower molecular weight polyalkylene polyamines, higher, non-cyclic polyalkylene polyamines, which are of enhanced commercial value.

We claim:

1. A method for reforming a feedstock of ethylene diamine or polyalkylene polyamine into a polyalkylene polyamine product different from said feedstock, said method comprising heating said feedstock with water and a catalyst to a temperature of 200°–400° C., in a reaction vessel, said catalyst comprised of a phosphate compound of a metal group consisting of boron and lithium, sodium, potassium, and other metals of group IA of the periodic table; beryllium, magnesium, calcium, and other metals of group IIA of the periodic table; zirconium, antimony, tin (valence states II and IV) and iron in both the ferrous and ferric states, said method comprising holding said feedstock with water and catalyst at said temperature for 0.5–5 hours, said proportion of catalyst and water with said feedstock, said feedstock temperature and said time of heating all being selected to cause conversion of said feedstock to a different polyalkylene polyamine product.

2. A method, as recited in claim 1, wherein said polyalkylene polyamine in said feedstock is a compound selected from the group consisting of, diethylene triamine and triethylene tetramine.

3. A method, as recited in claim 1, wherein said feedstock, water and catalyst are heated to 225°–350° C.

4. A method, as recited in claim 3, wherein said feedstock, water and catalyst are heated for 1 to 4 hours.

5. A method, as recited in claim 4, wherein said feedstock is a compound selected from the group consisting of ethylene diamine, diethylene triamine and triethylene tetramine.

6. A method, as recited in claim 1 or claim 5, wherein said catalyst is present in an amount of 5–8 mol percent based on the feedstock.

7. A method, as recited in claim 1 or claim 5, said catalyst being present in an amount of 1–10 mol percent based on the feedstock.

8. A method, as recited in any of claims 1 to 5, wherein said catalyst is boron phosphate.

9. A method, as recited in claim 6, wherein said catalyst is boron phosphate.

* * * * *